United States Patent
Gruhler

(10) Patent No.: US 9,719,834 B2
(45) Date of Patent: Aug. 1, 2017

(54) FILL-LEVEL MEASURING DEVICE

(71) Applicant: VEGA GRIESHABER KG, Wolfach (DE)

(72) Inventor: Holger Gruhler, Tuningen (DE)

(73) Assignee: VEGA GRIESHABER KG, Wolfach (DE)

( * ) Notice: Subject to any disclaimer, the term of this patent is extended or adjusted under 35 U.S.C. 154(b) by 70 days.

(21) Appl. No.: 14/786,391

(22) PCT Filed: May 15, 2014

(86) PCT No.: PCT/EP2014/059996
§ 371 (c)(1),
(2) Date: Oct. 22, 2015

(87) PCT Pub. No.: WO2014/184307
PCT Pub. Date: Nov. 20, 2014

(65) Prior Publication Data
US 2016/0069730 A1    Mar. 10, 2016

(30) Foreign Application Priority Data
May 15, 2013 (EP) .................................. 13167856

(51) Int. Cl.
*G01F 23/284* (2006.01)
*G01F 23/296* (2006.01)

(52) U.S. Cl.
CPC ........ *G01F 23/296* (2013.01); *G01F 23/2967* (2013.01); *G01F 23/2968* (2013.01);
(Continued)

(58) Field of Classification Search
CPC .................................................. G01F 23/2962
(Continued)

(56) References Cited

U.S. PATENT DOCUMENTS 4,703,652 A * 11/1987 Itoh ..................... G01F 23/2967
29/25.35
4,730,650 A * 3/1988 Ziegler ................... G01F 23/28
137/392

(Continued)

FOREIGN PATENT DOCUMENTS

DE         100 23 302 C2     5/2000
DE     10 2004 033 311 A1    8/2004
(Continued)

OTHER PUBLICATIONS

Searching Authority (ISA), Written Opinion ISA PCT/EP2014/059996, Fill-Level Measuring Device, May 15, 2013, 6 pp.*
(Continued)

*Primary Examiner* — Clayton E Laballe
*Assistant Examiner* — Kevin Butler
(74) *Attorney, Agent, or Firm* — Juneau & Mitchell

(57) ABSTRACT

The invention is a fill-level measuring device having the following features: a housing, a membrane, a first drive unit have a first bolt, the bolt being coupled to the membrane, a second drive unit having a second bolt, the second bolt being operatively connected to the membrane and being connected to the housing at an end of the second bolt facing the membrane by means of an intermediate bottom, and the first drive unit and the second drive unit are mechanically connected to each other in series.

11 Claims, 5 Drawing Sheets

(52) U.S. Cl.
CPC ........ *G01F 23/284* (2013.01); *G01F 23/2962* (2013.01); *G01N 2291/02836* (2013.01)

(58) Field of Classification Search
USPC ...................................... 73/290 V
See application file for complete search history.

(56) References Cited

U.S. PATENT DOCUMENTS

| | | | | |
|---|---|---|---|---|
| 8,752,426 | B2* | 6/2014 | Wimberger | G01D 21/02 73/290 R |
| 2002/0014117 | A1* | 2/2002 | Raffalt | G01F 23/2967 73/290 V |
| 2009/0071246 | A1* | 3/2009 | Gruhler | G01F 23/296 73/290 V |
| 2011/0226064 | A1* | 9/2011 | Dreyer | G01F 23/2967 73/632 |
| 2012/0103088 | A1* | 5/2012 | Urban | G01F 23/2967 73/290 V |
| 2012/0279283 | A1* | 11/2012 | Brengartner | G01F 23/2961 73/54.41 |
| 2015/0047428 | A1* | 2/2015 | Lopatin | G01F 25/0061 73/290 V |
| 2015/0068300 | A1* | 3/2015 | Pfeiffer | G01F 23/2967 73/290 V |
| 2016/0069730 | A1* | 3/2016 | Gruhler | G01F 23/2968 73/290 V |

FOREIGN PATENT DOCUMENTS

DE  10 2007 041 349 A1  8/2007
DE  10 2008 043 764 A1  11/2008

OTHER PUBLICATIONS

Searching Authority (ISA), Search Report PCT/EP2014/059996, Fill-Level Measuring Device, Nov. 13, 2013, 3 pp.*
International Search Report issued in corresponding PCT Application No. PCT/EP2014/05996, Sep. 13, 2015.

* cited by examiner

FILL-LEVEL MEASURING DEVICE

CROSS REFERENCE TO RELATED APPLICATIONS

This patent application claims priority to International Patent Application PCT/EP2014/059996, filed on May 15, 2014, and thereby to European Patent Application 13167856.7, filed on May 15, 2013.

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT

Not applicable.

SEQUENCE LISTING INCLUDED AND INCORPORATED BY REFERENCE HEREIN

Not applicable.

BACKGROUND

Field of the Invention

The invention relates to fill level measuring device with a membrane and a drive unit actuating this membrane, whereby oscillating rods are molded onto the membrane at regular intervals.

Background of the Invention

Fill level measuring devices are known, for example, from German Patent DE 100 23 302 C2. A stack of piezoelectric elements with a tension bolt for actuating the piezoelectric elements serves as the drive unit. The stack of piezoelectric elements is disposed between a preload element, in particular a preload nut, and a pressure ring in contact with the membrane. Even though these fill level measuring devices are perfectly suitable to determine fill levels, one drawback of this type of drive lies in that the preloaded drive stack of piezoelectric elements is released at positive process pressure (excess pressure) due to the distending membrane and the off-center pressure ring. As a result, the mechanical coupling of the piezoelectric elements decreases as the process pressure increases. Such low mechanical coupling leads to decreasing electric amplitudes, which can even lead to complete failure of the drive unit. This effect can be offset by applying a higher bias voltage to the piezoelectric elements, but this is possible only to a limited extent, because the individual piezoelectric elements have a mechanical load limit, resulting in an increased risk of breaking if the bias voltage is too high, and also, if the pressure is too great, depolarization occurs. A further problem is that a higher bias voltage of the drive unit causes structural mechanical stiffening of the membrane.

In order to avoid this disadvantage, i.e. to avoid a release of the stack under positive process pressure, vibration limit switches with a bolted, piezoelectric drive are now also being sold by the applicant, whereby the drive is braced on an intermediate bottom attached to the pipe wall of the housing of the fill level measuring device. Such fill level measuring devices are disclosed, for example, in DE 10 2007 041 349 A1. The bolt in this fill level measuring device no longer functions as a tension bolt, but rather as a pressure bolt. On its end facing the membrane, this pressure bolt is fixedly connected to the aforementioned intermediate bottom, and at its upper end it is provided with a preload element, in particular a preload nut, via which the stack of piezoelectric elements can be pushed toward the center of the membrane, against a pressure piece reaching through the intermediate bottom. Such an arrangement of the fill level measuring device has the advantage that the entire drive unit is loaded with positive process pressure. The electrical amplitude therefore does not decrease with increasing pressure, as is the case in the fill level measuring devices mentioned above.

In this second type of drive, however, it is disadvantageous that the stack of piezoelectric elements is now released at negative process pressure (vacuum). Since the drive side of the membrane is usually under atmospheric pressure, the amount of negative process pressure is physically limited to −1 bar. Assuming thin membranes, however, which would be absolutely necessary, for example, when reducing the size of the fill level measuring device, even this pressure can already lead to a release of the drive. This release of the drive can even occur in applications with higher temperatures, because the axial extension of the bolt here causes additional release.

The objective of the invention is to specify a fill level measuring device that effectively avoids the disadvantages associated with the known fill level measuring devices. The sought after fill level measuring device should be configured in such a way that a sufficiently high electrical signal amplitude is supplied at both positive and negative process pressures, and that the entire assembly thus remains functional.

This task is solved by means of a fill level measuring device described herein.

BRIEF SUMMARY OF THE INVENTION

In a preferred embodiment, a fill level measuring device comprising the following features:
on the housing (1),
a membrane (3),
a first drive unit (10) with a first tension bolt (12) coupled to the membrane (3),
a second drive unit (30) with a pressure second bolt (32) coupled to the membrane (3), a second drive unit (30) with a second bolt (32), which on the bottom side is connected to an outer periphery of the membrane via an intermediate bottom and the housing, as well as on its upper end is attached to the center of the membrane via a preload element and a pressure piece reaching through the intermediate bottom, and
the first drive unit (10) and the second drive unit (30) are mechanically connected to one another in series.

In another preferred embodiment, the fill level measuring device as described herein, wherein the first drive unit (10) comprises:
a first stack with piezoelectric elements (17), which on the bottom side is mechanically coupled to the membrane (3) via a first pressure piece (14) that engages the membrane (3) off-center, and
wherein the first tension first bolt (12) is disposed centrally fixed on the membrane (3) and reaches through the first stack (16) and is tensioned against the first stack (16) via a first preload element (18) on the cover side.

In another preferred embodiment, the fill level measuring device as described herein, wherein the second drive unit (30) provides the following:

a second stack (36) with piezo-electric elements (37), which on the bottom side is mechanically coupled to the membrane (3) via a second pressure piece 14 that engages the membrane (3) centrally, the pressure second bolt (32) is fixedly connected to an intermediate bottom (31) fixed in the fill level measuring device and reaches through the second stack (36) and is tensioned against the second stack 36 via a second preload element (38) on the cover side.

In another preferred embodiment, the fill level measuring device as described herein, wherein the second stack (36) sits above the first stack (16).

In another preferred embodiment, the fill level measuring device as described herein, wherein the second pressure piece (34) is mechanically fixed to the first preload element (18).

In another preferred embodiment, the fill level measuring device as described herein, wherein the second pressure piece (34) reaches through or reaches over the intermediate bottom (31).

In another preferred embodiment, the fill level measuring device as described herein, wherein the intermediate bottom (31) is configured as an intermediate bottom plate and is attached to the housing (1), or to a part of the filling fill level measuring device fixed to the housing.

In another preferred embodiment, the fill level measuring device as described herein, wherein the first stack (16) sits above the second stack (36).

In another preferred embodiment, the fill level measuring device as described herein, wherein the first pressure piece (14) reaches over the second stack (36).

In another preferred embodiment, the fill level measuring device as described herein, wherein the tension first bolt (12) and the pressure second bolt (32) are arranged at least in sections to be coaxial to one another.

In another preferred embodiment, the fill level measuring device as described herein, wherein the first stack (16) and the second stack (36) are coaxially arranged to one another.

DETAILED DESCRIPTION OF THE INVENTION

The invention is substantially based on providing a fill level measuring device with the following characteristics:
 a housing,
 a membrane, a first drive unit with a first bolt coupled to the membrane, a second drive unit with a second bolt operatively connected to the membrane, which on its end facing the membrane (3) is connected to the housing via an intermediate bottom (31) and the first drive unit and the second drive unit are mechanically connected to one another in series.

The underlying idea of the present invention is therefore to combine the previously known two drive concepts with one another, and to do it in such a way that the two drive concepts are mechanically connected in series. The result is that, at both positive and negative process pressures, one of the two drive units is always under mechanical load and the other is mechanically released. There is therefore always one available functioning drive.

Therefore, at positive process pressure for example, the drive unit that is released under external positive pressure would become inoperative, i.e. the drive unit with the second bolt. In this case, however, the drive unit with the first bolt is more heavily loaded, thus enabling the overall measuring device to remain functional.

In the opposite case, i.e. at negative process pressure, on the other hand, the first drive unit with its first bolt remains functional and the second drive unit with the second bolt can become inoperative. The drive overall nonetheless remains functional.

Electrically, the two drive units can be operated together, and thus in parallel, by one control electronics unit, so that the cumulative amplitude of the two drive units is always sufficiently large across a wider pressure range.

It is also within the scope of the invention, however, for the two drive units to be operated separately with different control circuits, in which case all that remains is to logically link the results.

According to the present invention, it is only necessary to mechanically connect the first drive unit and the second drive unit in series. This can be done either by disposing the first drive unit above the second drive unit, the second drive unit above the first drive unit, or by arranging the two drive units coaxially to one another.

DETAILED DESCRIPTION OF THE FIGURES

Figure 1:
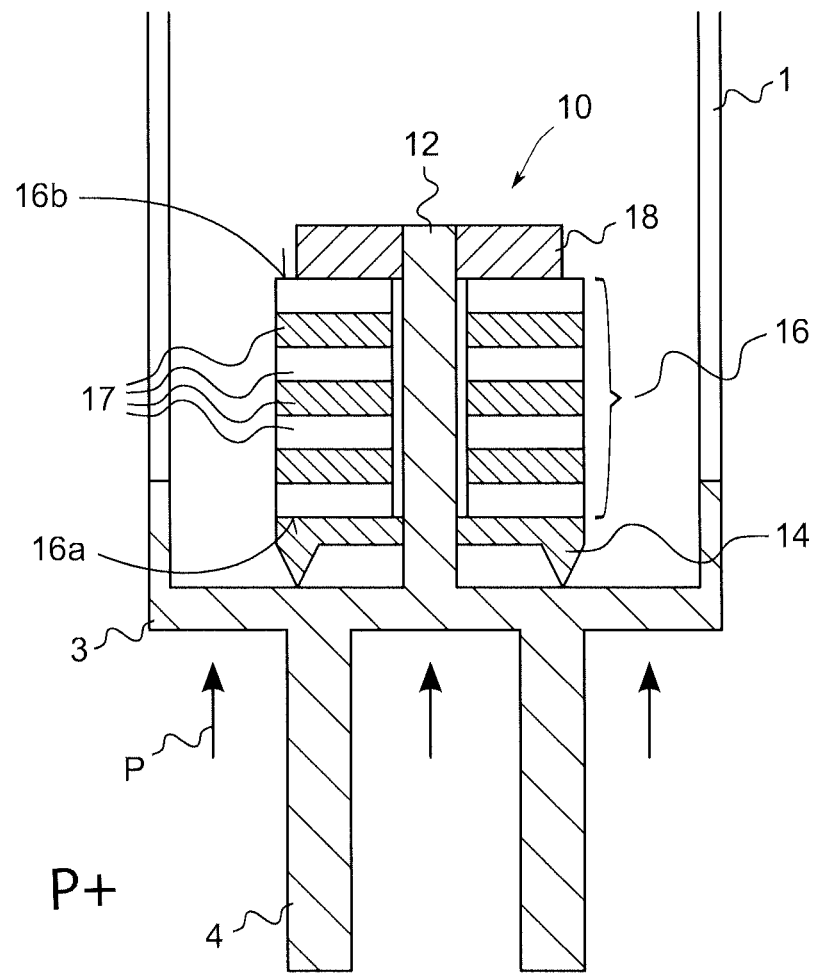
FIG. 1 is a line drawing evidencing the basic structure in a sectional view of a known fill level measuring device with a drive unit and tension bolts.

FIG. 1 shows the basic structure of a known fill level measuring device, with a drive unit and a first bolt which acts as a tension bolt, in a sectional view. Such a fill level measuring device is known from DE 100 23 302 C2, for example, so that therefore only the essential components of the fill level measuring device have to be addressed in connection with FIG. 1.

The device comprises a cylindrical housing 1 which is closed at its bottom with a membrane 3. The membrane is preferably connected on a side facing away from the interior of the pot of the housing 1 in a known manner to two fork tines 4. In the interior of the housing 1 there is a first drive unit 10, which in the present case exhibits a first bolt 12, here a tension bolt, that is affixed in one piece in the center of the membrane 3 by its lower end. A first stack 16 of piezoelectric elements 17 is disposed around the first bolt 12. The individual piezoelectric elements 17 will preferably not be in contact with the tension bolt 12 on their coaxial inner sides. The first stack 16 of piezoelectric elements 17, which can of course also be replaced by other suitable drive elements, exhibits a lower bottom side 16a, facing the membrane 3, and an opposite upper side 16b. Between the bottom side 16a and the membrane 3, there is a first pressure piece 14, on which the entire first stack 16 is seated in an annular manner on the upper side of the membrane 3. On the upper, free end of the first bolt 12, there is a first preload element 18, in this case a preloading screw, via which pressure can be applied to the upper side 16b and thus to the entire first stack upon rotation of the preload element 18, so that preloading on the membrane 3 can be adjusted.

Such a fill level measuring device is preferably used as a vibration point level sensor and is also ideally suited for this purpose. At positive process pressure (excess pressure), however, this positive process pressure causes the membrane 3 in the area of the fork tines 4 to bulge upwards into the interior of the housing 1, and thus in the direction of the first drive unit 10. This positive process pressure is indicated in FIG. 1 with P+. The arrows in the direction of membrane 3 indicate that, at positive pressure P+, the membrane bulges in upward direction, i.e. into the interior of the housing 1. With increasing positive process pressure P, this positive process pressure P+, with the associated bulging of the membrane 3, can lead to a weaker mechanical coupling of the piezoelectric elements 17, which is of course undesirable. At negative process pressure P−, the membrane 3 bulges in the opposite direction and the mechanical coupling is improved.

Figure 2:
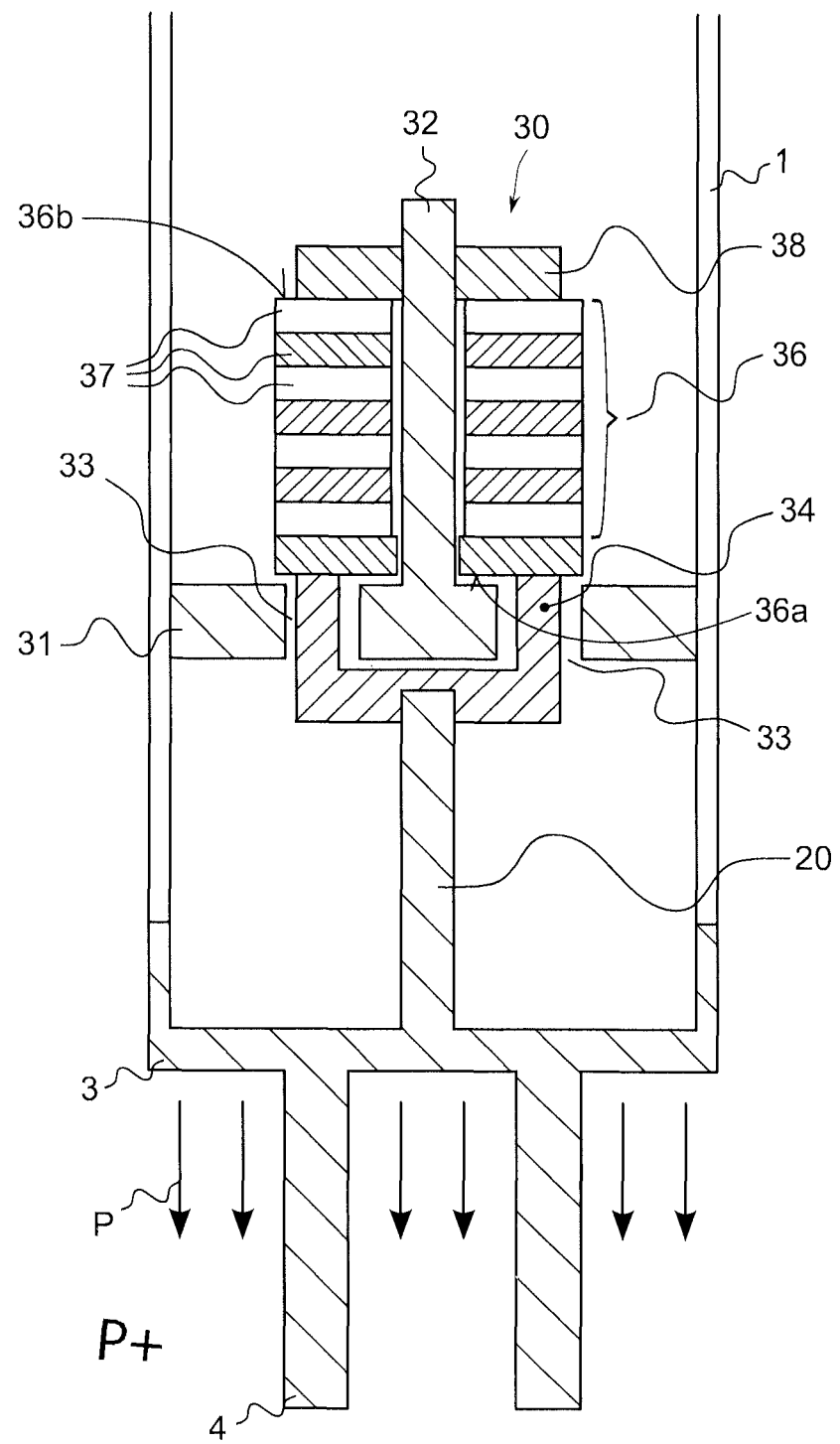
FIG. 2 is a line drawing evidencing the basic structure in a sectional view of a known fill level measuring device with a drive unit and bolts, as well as an associated intermediate bottom.

A second fill level measuring device, which is known per se and also described in detail in DE 10 2007 041 349 AI, for example, is shown in FIG. 2. As indicated by the arrows in FIG. 2, at positive process pressure P+ the membrane 3 is not distended into the interior of the housing 1, but rather in the direction of the fork tines 4.

The basic structure of this known fill level measuring device again exhibits a pot-shaped housing 1, on the underside of which the membrane 3 is fixedly mechanically connected with fork tines 4. In the interior of the housing, the center of the membrane is provided with a bolt piece 20 which extends into the housing 1. A second drive unit 30 is coupled onto the upper end of this bolt piece 20, whereby, for this purpose, an intermediate bottom 31 that is preferably orthogonal to the walls of the housing 1 is provided. Openings 33 are provided in this intermediate bottom 31 through which a U-shaped pressure piece 34 reaches, that is affixed to the upper end of the bolt piece 20 with its underside. A stack 36 of piezoelectric elements 37 is seated on the upper side of the second pressure piece 34. This stack 36 with its piezoelectric elements 37 is in turn disposed coaxially around a second [sic] 32. This second bolt 32 is centrally affixed at its lower end on the intermediate bottom 31. At the upper end of this second bolt 32 there is in turn a preload element 38, which is preferably a preload nut or a preloading screw, via which the upper side 36b of the stack 36 of piezoelectric elements 37 can be pushed against the second pressure piece 34. For this purpose, the stack 36 of piezoelectric elements 37 rests with its bottom side 36a on the pressure piece 34. Therefore, overall, the second bolt 32 is also in operative connection to the membrane 3. In the arrangement of FIG. 2, the drive unit 30 in the unpressurized state, i.e. the pressure outside the housing 1 is equal to the pressure inside the housing 1 of the fill level measuring device, is placed under pressure via the second preload element 38, i.e. the second bolt 32 is under tension. At positive process pressure P+ outside the housing 1, i.e. pressure that is greater outside the housing 1 than it is within the housing 1, this results in the entire drive 30 of FIG. 2 being loaded further; increasing the mechanical coupling of the piezoelectric elements 37 even more, which is desired. At negative process pressure on the other hand, the membrane 3 bulges inward into the housing 1 and the mechanical coupling of the piezoelectric elements 37 is reduced. In this known fill level measuring device, which is likewise preferably used as a vibration point level sensor, the disadvantage described in connection with FIG. 1 is indeed avoided. However, at negative process pressure (vacuum), the stack 36 of piezoelectric elements 37 is relieved, which is in itself a disadvantage.

Figure 3:
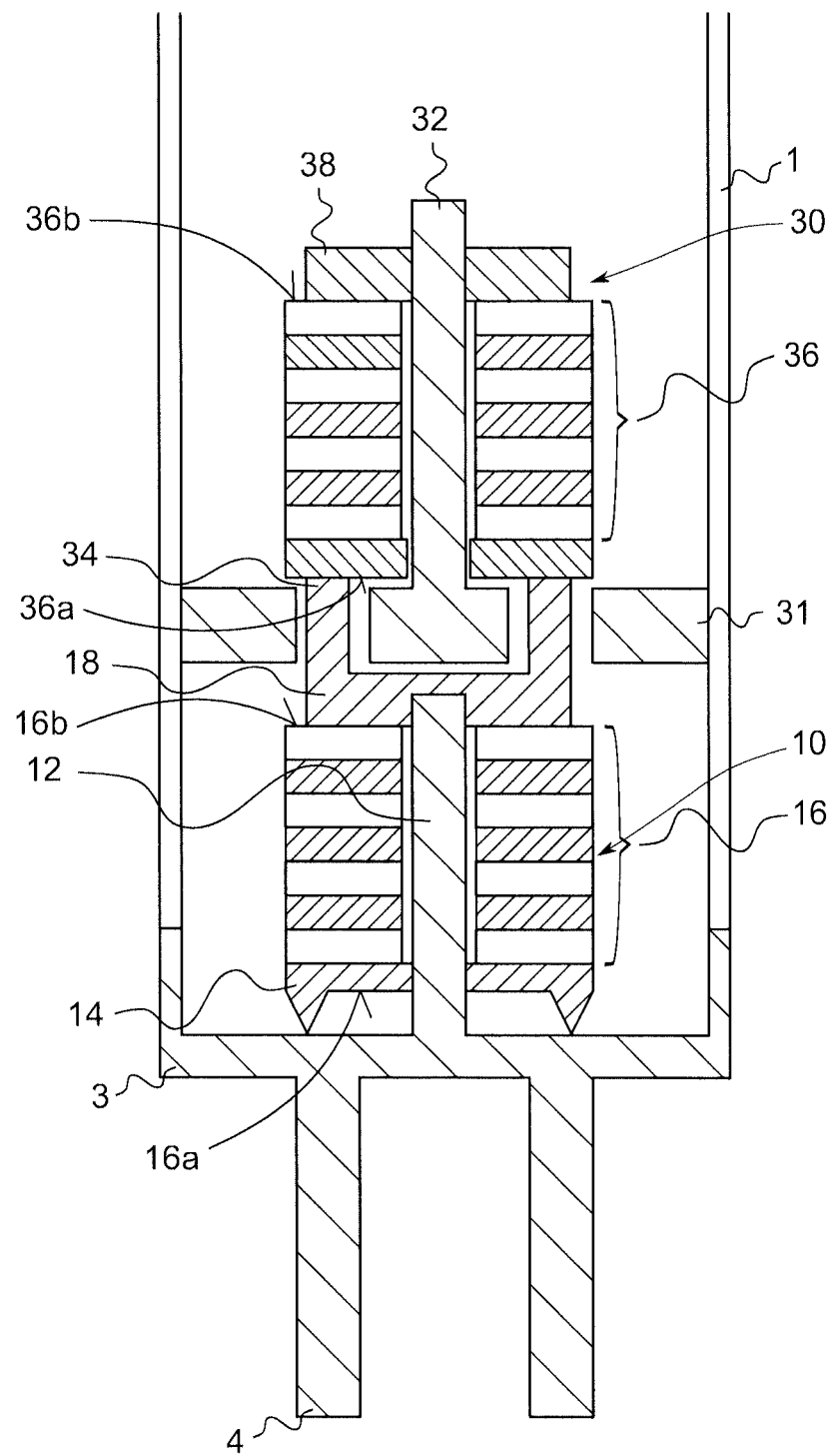
FIG. 3 is a line drawing evidencing a first design example of a fill level measuring device according to the invention, in which the second drive unit according to FIG. 2 is disposed above the first drive unit according to FIG. 1.

FIG. 3 shows a first design example of a fill level measuring device according to the invention, in which again a membrane 3 with fork tines 4 and a housing 1 are provided. In this fill level measuring device according to the invention, however, the concept of the drive units from the previously described fill level measuring devices are combined with one another. This means that a first drive unit 10, with a first bolt 12 coupled to the membrane 3, as well as a second drive unit 30, with a second bolt 32 coupled to the membrane 3, are provided inside the housing. The first drive unit 10 and the second drive unit 30 are mechanically connected to one another in series. In the design example of FIG. 3, the fill level measuring device described in connection with FIG. 2 is positioned above the fill level measuring device shown in FIG. 1. The already known reference signs continue to stand for the same parts.

A particular structural configuration results from the fact that the upper end of the first bolt 12 is still connected to the first preload element 18, in other words a preloading screw. This first preload element 18, however, simultaneously functions as the second pressure piece 34. For this purpose the second pressure piece 34 is fixedly connected to the first preload element 18.

The arrangement of a fill level measuring device shown in FIG. 3 is again preferably used as a vibration point level sensor, and has the major advantage that a sufficient electrical amplitude is supplied at both positive and negative process pressures, whereby the overall assembly remains functional. Both at positive as well as at negative process pressure one of the two stacks 16, 36 is always mechanically loaded and the other stack 36, 16 is mechanically released. Therefore, there is always a functional drive unit 10 or 30 available. Even though the lower drive unit 10 is released under positive process pressure, which can ultimately lead to functional failure of the first drive unit 10, the second stack 36 of piezoelectric elements 37, positioned above it, is loaded, so that the second drive unit 30 most certainly remains operative.

If there is negative process pressure, on the other hand, the first drive unit 10 is loaded and thus remains in operation, while the second drive unit 30 is released, and may even become inoperative. The overall drive unit nonetheless remains functional, because, according to the structural design of the mechanical in-series circuit, when one of the two drive units 10, 30 become inoperative, an additional, redundant drive is always available.

As explained, the fill level measuring device of FIG. 3 is designed in such a way that one of the drives 16, 36 is always released and the other drive 16, 36 is loaded when positive pressure is applied. This is illustrated one more time in the following table. This is independent of the sign of the acting process pressure. One of the two drives 16, 36 is always increasingly loaded and the other drive 16, 36 is increasingly released.

| Pressure P | Membrane bulges in FIG. 3 | First drive unit 10 | Second drive unit 30 |
| --- | --- | --- | --- |
| positive P+ | upward | is released | is loaded |
| negative P− | downward | is loaded | is released |

If the process pressure outside the housing 1 is identical to the pressure within the housing 1 of fill level measuring device, the membrane is not distended. The two piezoelectric stacks 16, 36 of the first drive unit 10 and the second drive unit 30 are put under pressure via the respective preload elements 18, 38, so that both the first bolt 12 and the second bolt 22 are under tension. A difference in the load of the two stacks 16, 36, and with that also whether the first bolt 12 and second bolt 32 are under tension or pressure loaded, comes into being only as a result of the effective direction of the applied process pressure P.

Electrically the two drive units 10, 30 can be operated together, i.e. in parallel, by one common control electronics unit, so that the cumulative amplitude of the two drive units 10, 30 is always sufficiently large across a wide pressure range. It is also possible, however, to operate the two drive units 10, 30 with separate control units. The output signals of the drive units 10, 30 then only have to be appropriately logically linked to one another.

Figure 4:
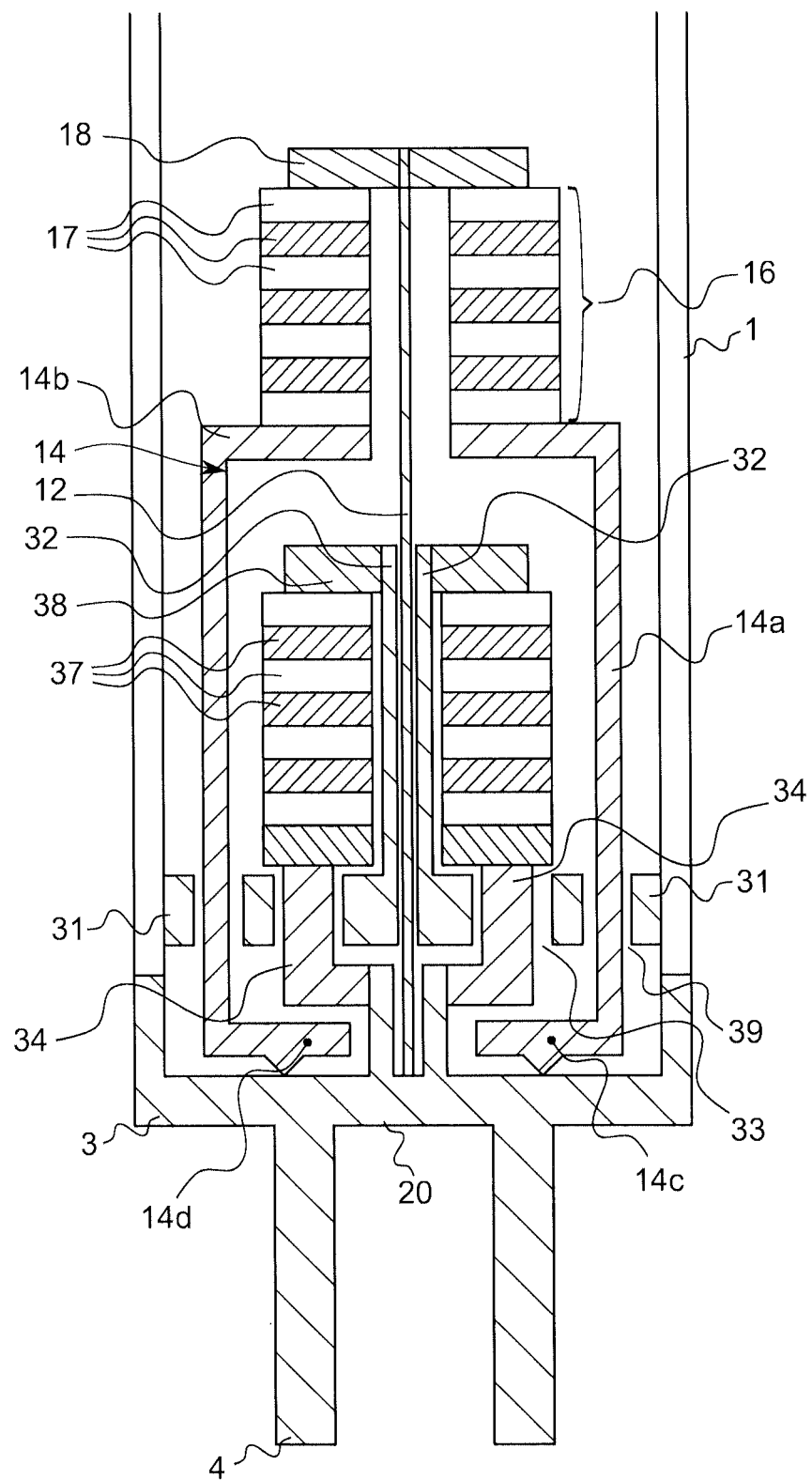
FIG. 4 is a line drawing evidencing a second design example of a fill level measuring device according to the invention, in which the drive unit known from FIG. 1 is disposed above the drive unit known from FIG. 2.

The design example of FIG. 4 shows a second design example for a fill level measuring device according to the present invention. Now, however, the first drive unit 10 with the first bolt 12 is positioned above the second drive unit 30 with the second bolt 32. The second drive unit 30 is in operative connection with the membrane 3, similar to how it is shown in FIG. 2. Aside from the openings 33 for the second pressure piece 34, however, the intermediate bottom 31 has additional openings 39 to hold wall sections 14a of the first pressure piece 14 in a yet to be explained manner. Furthermore, in contrast to the illustration of FIG. 2, both the bolt piece 20 and the second bolt 32 are configured as a hollow wall pipe, so as to be able to catch the first bolt 12 of the first drive unit 10, which in this design example is positioned above the second drive unit 30. This first bolt 12 is centrally affixed on the upper side of the membrane 3 by its lower end and protrudes through the bolt piece 20 and the second bolt 32. At its upper end this first bolt 12 is in turn connected to a first preload element 18, preferably a preload nut, so as to push the first stack 16 of piezoelectric elements 17 against the membrane 3 via the specially designed first pressure piece 14.

The first pressure piece 14 has wall sections 14a extending parallel to the housing 1, which surround the second drive unit 30 and at its upper end drop it below a plate-shaped element 14b on which the stack 16 of piezoelectric elements 17 is seated. At their lower end, the wall sections 14a, which reach through the mentioned openings 39 into the intermediate bottom 31, are in turn closed by an element which is, however, ring-shaped. This annular element is identified by the reference sign 14c. The central opening of this annular element 14c surrounds the bolt piece 20 and has, on its side facing the membrane 3, an in cross section conically tapering pressure ring section 14d, via which, with respective preloading of the first preload element 18, corresponding pressure can be exerted on the upper side of the membrane 3.

In the arrangement shown in FIG. 4, the first drive unit 10 with the first bolt 12 is therefore positioned above the second drive unit 30 with the second bolt 32.

Figure 5:
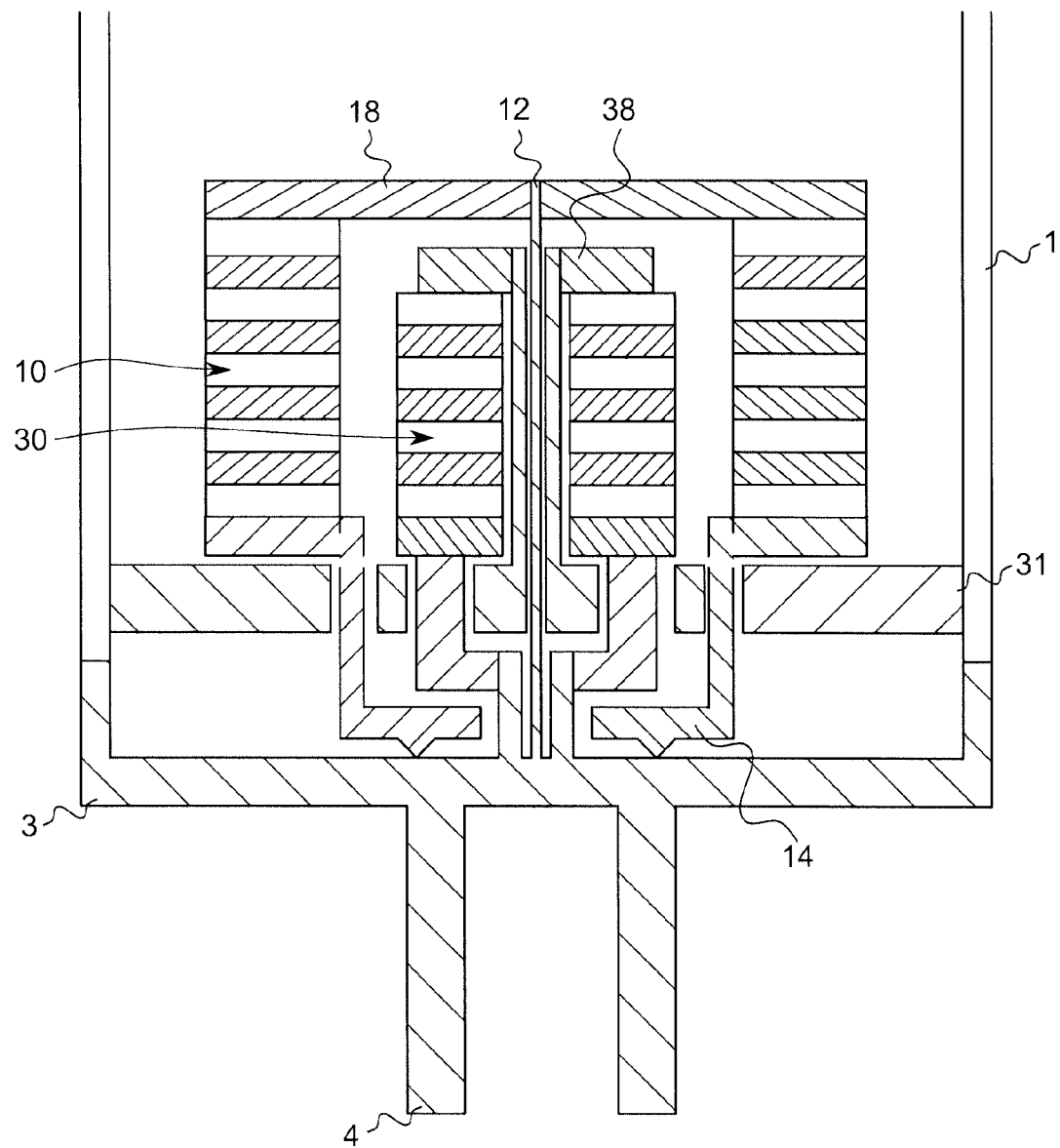
FIG. 5 is a line drawing evidencing a third design example of the invention, in which the first drive unit and the second drive unit are coaxially arranged to one another.

FIG. 5 lastly shows a third design example of a fill level measuring device according to the invention. In this fill level measuring device, the first drive unit 10 and the second drive unit 30 are positioned coaxially to one another. The arrangement largely corresponds to the arrangement of FIG. 4. However, the individual piezoelectric elements of the first elements 17 of the first stack 16 of the first driving unit 10 are now configured in such a way that they can be coaxially disposed around the second drive unit 30. The diameter of the first preload element 18 must be configured to be correspondingly large.

With this arrangement too, the situation is such that a fill level measuring device is provided, with a membrane 3, in which the first drive unit 10 with a first bolt 12 coupled to the membrane 3, as well as a second drive unit with a second bolt in operative connection with the membrane 3, is provided. The first drive unit 10 and the second drive unit 30 are likewise mechanically connected in series.

LIST OF REFERENCE NUMBERS

1 Housing
3 Membrane
4 Fork tines
10 First drive unit
12 First bolt
14 First pressure piece
14a Wall sections
14b Plate shaped element
14c Annular element
14d Pressure ring section
16 First stack
16a Bottom side
16b Upper side
17 Piezoelectric elements
18 First preload element
20 Bolt piece
30 Second drive unit
31 Intermediate bottom
32 Second bolt
33 Openings in the intermediate bottom
34 Second pressure piece
36 Second stack
36a Bottom side
36b Upper side
37 Piezoelectric elements
38 Second preload element
39 Opening The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

The invention claimed is:

1. A fill level measuring device comprising the following features:
   on the housing,
   a membrane,
   a first drive unit with a first tension bolt coupled to the membrane,
   a second drive unit with a pressure second bolt coupled to the membrane, a second drive unit with a second bolt, which on the bottom side is connected to an outer periphery of the membrane via an intermediate bottom and the housing, as well as on its upper end is attached to the center of the membrane via a preload element and a pressure piece reaching through the intermediate bottom, and
   the first drive unit and the second drive unit are mechanically connected to one another in series.

2. The fill level measuring device of claim 1, wherein the first drive unit comprises:

a first stack with piezoelectric elements, which on the bottom side is mechanically coupled to the membrane via a first pressure piece that engages the membrane off-center, and wherein the first tension first bolt is disposed centrally fixed on the membrane and reaches through the first stack and is tensioned against the first stack via a first preload element on the cover side.

3. The fill level measuring device of claim 2, wherein the second drive unit provides the following:
a second stack with piezo-electric elements, which on the bottom side is mechanically coupled to the membrane via a second pressure piece that engages the membrane centrally, the pressure second bolt is fixedly connected to an intermediate bottom fixed in the fill level measuring device and reaches through the second stack and is tensioned against the second stack via a second preload element on the cover side.

4. The fill level measuring device of claim 3, wherein the second stack sits above the first stack.

5. The fill level measuring device of claim 4, wherein the second pressure piece is mechanically fixed to the first preload element.

6. The fill level measuring device of claim 3, wherein the second pressure piece reaches through or reaches over the intermediate bottom.

7. The fill level measuring device of claim 3, wherein the intermediate bottom is configured as an intermediate bottom plate and is attached to the housing, or to a part of the filling fill level measuring device fixed to the housing.

8. The fill level measuring device of claim 3, wherein the first stack and the second stack are coaxially arranged to one another.

9. The fill level measuring device of claim 1, wherein the first stack sits above the second stack.

10. The fill level measuring device of claim 9, wherein the first pressure piece reaches over the second stack.

11. The fill level measuring device of claim 1, wherein the tension first bolt and the pressure second bolt are arranged at least in sections to be coaxial to one another.

* * * * *